United States Patent
Goshen et al.

(10) Patent No.: US 10,646,185 B2
(45) Date of Patent: May 12, 2020

(54) IFR-CT

(71) Applicant: KONINKLIJKE PHILIPS N.V., Eindhoven (NL)

(72) Inventors: Liran Goshen, Pardes-Hanna (IL); Yechiel Lamash, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 235 days.

(21) Appl. No.: 15/542,451

(22) PCT Filed: Jan. 6, 2016

(86) PCT No.: PCT/IB2016/050043
§ 371 (c)(1),
(2) Date: Jul. 10, 2017

(87) PCT Pub. No.: WO2016/113646
PCT Pub. Date: Jul. 21, 2016

(65) Prior Publication Data
US 2018/0271468 A1    Sep. 27, 2018

Related U.S. Application Data

(60) Provisional application No. 62/103,721, filed on Jan. 15, 2015.

(51) Int. Cl.
*G06T 7/62* (2017.01)
*G06T 7/00* (2017.01)
(Continued)

(52) U.S. Cl.
CPC .......... *A61B 6/507* (2013.01); *A61B 5/02007* (2013.01); *A61B 5/7271* (2013.01);
(Continued)

(58) Field of Classification Search
None
See application file for complete search history.

(56) References Cited

U.S. PATENT DOCUMENTS 8,157,742 B2    4/2012 Taylor
8,200,466 B2    6/2012 Spilker
(Continued)

FOREIGN PATENT DOCUMENTS

DE    102008014792    6/2009
EP    2942006    11/2015
(Continued)

OTHER PUBLICATIONS

Taylor, et al., "Computational Fluid Dynamics Applied to Cardiac Computed Tomography for Noninvasive Quantification of Fractional Flow Reserve", Journal of the American College of Cardiology, vol. 61, No. 22, Jun. 1, 2013.
(Continued)

*Primary Examiner* — Nancy Bitar
(74) *Attorney, Agent, or Firm* — Larry Liberchuk

(57) ABSTRACT

A method includes for non-invasively determining an instantaneous wave-free ratio metric includes receiving electronically formatted image data generated by an imaging system. The image data includes voxels with intensities representative of a vessel with a stenosis. The method further includes computing peripheral resistances of outlets of the vessel from the image data. The method further includes calculating a stenosis resistance of the stenosis between an inlet of the vessel inlet and the outlets of the vessel based on a set of boundary conditions and a computational fluid dynamics algorithm. The method further includes calculating the instantaneous wave-free ratio metric. The metric is a
(Continued)

numerical value, based on the stenosis resistance and generating a signal indicative of the calculated instantaneous wave-free ratio metric.

20 Claims, 3 Drawing Sheets

(51) Int. Cl.

| | |
|---|---|
| *G16H 50/50* | (2018.01) |
| *A61B 6/00* | (2006.01) |
| *A61B 5/00* | (2006.01) |
| *A61B 5/02* | (2006.01) |
| *G16H 30/20* | (2018.01) |
| *A61B 6/03* | (2006.01) |
| *A61B 5/026* | (2006.01) |

(52) U.S. Cl.
CPC .............. *A61B 6/032* (2013.01); *A61B 6/504* (2013.01); *A61B 6/5217* (2013.01); *G06T 7/0012* (2013.01); *G06T 7/62* (2017.01); *G16H 30/20* (2018.01); *A61B 5/026* (2013.01); *A61B 5/02028* (2013.01); *A61B 6/03* (2013.01); *G06T 2207/10081* (2013.01); *G06T 2207/30104* (2013.01); *G16H 50/50* (2018.01)

(56) References Cited

U.S. PATENT DOCUMENTS

| | | | |
|---|---|---|---|
| 8,249,815 B2 | 8/2012 | Taylor | |
| 9,135,699 B2* | 9/2015 | Ralovich | G06T 7/0012 |
| 9,138,147 B2* | 9/2015 | Schmitt | A61B 5/0066 |
| 10,258,303 B2* | 4/2019 | Grass | A61B 6/504 |
| 2010/0125197 A1 | 5/2010 | Fishel | |
| 2010/0130878 A1 | 5/2010 | Lasso | |
| 2010/0241404 A1 | 9/2010 | Taylor | |
| 2011/0211742 A1 | 9/2011 | Bredno | |
| 2011/0307231 A1 | 12/2011 | Kirchner | |
| 2012/0022843 A1 | 1/2012 | Ionasec | |
| 2012/0041318 A1 | 2/2012 | Taylor | |
| 2012/0041319 A1 | 2/2012 | Taylor | |
| 2012/0041320 A1 | 2/2012 | Taylor | |
| 2012/0041321 A1 | 2/2012 | Taylor | |
| 2012/0041322 A1 | 2/2012 | Taylor | |
| 2012/0041323 A1 | 2/2012 | Taylor | |
| 2012/0041324 A1 | 2/2012 | Taylor | |
| 2012/0041325 A1 | 2/2012 | Taylor | |
| 2012/0041739 A1 | 2/2012 | Taylor | |
| 2012/0053918 A1 | 3/2012 | Taylor | |
| 2012/0053919 A1 | 3/2012 | Taylor | |
| 2012/0059246 A1 | 3/2012 | Taylor | |
| 2012/0072190 A1 | 3/2012 | Sharma | |
| 2012/0121151 A1 | 5/2012 | Bernhardt | |
| 2012/0243761 A1 | 9/2012 | Senzig | |
| 2012/0296199 A1 | 11/2012 | Kim | |
| 2014/0073977 A1* | 3/2014 | Grady | A61B 5/7267 600/504 |
| 2014/0114618 A1 | 4/2014 | Fonte | |
| 2014/0249784 A1 | 9/2014 | Sethuraman | |
| 2014/0276137 A1 | 9/2014 | Burnett | |
| 2015/0374243 A1* | 12/2015 | Itu | G16H 50/50 703/2 |
| 2016/0022371 A1* | 1/2016 | Sauer | A61B 6/504 600/407 |
| 2017/0323177 A1* | 11/2017 | Sauer | A61B 34/10 |

FOREIGN PATENT DOCUMENTS

| | | |
|---|---|---|
| WO | 00/72037 | 11/2000 |
| WO | 2004025572 | 3/2004 |
| WO | 200661814 | 6/2006 |
| WO | 2006061815 | 6/2006 |
| WO | 201022762 | 3/2010 |
| WO | 2013171644 | 11/2013 |
| WO | 2014/002095 | 1/2014 |
| WO | 2014072861 | 5/2014 |
| WO | 2016001017 | 1/2016 |

OTHER PUBLICATIONS

Sen, et al., "Development and Validation of a New Adenosine-Independent Index of Stenosis Severity from Coronary Wave-Intensity Analysis", Journal of the American College of Cardiology, vol. 59, No. 15, Apr. 1, 2012.
Koo, "The Present and Future of Fractional Flow Reserve", Circulation Journal, vol. 78, No. 5, Jan. 1, 2014.
Kochar, et al., "Physiologic Assessment of Coronary Artery Disease by Cardiac Computed Tomography", Korean Circulation Journal, vol. 43, No. 7, Jan. 1, 2013.
Bjarne, et al., "Diagnostic Performance of Noninvasive Fractional Flow Reserve Derived from Coronary Computed Tomography Angiography in Suspected Coronary Artery Disease the NXT Trial (Analysis of Coronary Blood Flow Using CT Angiography: Next Steps)", Journal of the American College of Cardiology, vol. 63, No. 12, Dec. 31, 2014.
Koo, et al., "Diagnosis of Ischemia-Causing Coronary Stenoses by Noninvasive Fractional Flow Reserve Computed from Coronary Computed Tomographic Angiograms", Journal of the American College of Cardiology, vol. 58, No. 19, Nov. 1, 2011.
Pijls, et al. "Fractional flow reserve. A useful index to evaluate the influence of an epicardial coronary stenosis on myocardial blood flow", Circulation. 1995; 92: 3183-3193.
Pijls, et al., "Measurement of fractional flow reserve to assess the functional severity of coronary-artery stenoses" N. Engl. J. Med. 334 (26): 1703-8, Jun. 1996.
Kern, et al., "Current concepts of integrated coronary physiology in the catheterization laboratory", J Am Coll Cardiol. 2010;55:173-185.
Sen, Sayan, et al. "Diagnostic classification of the instantaneous wave-free ratio is equivalent to fractional flow reserve and is not improved with adenosine administration: results of CLARIFY (Classification Accuracy of Pressure-Only Ratios Against Indices Using Flow Study)" Journal of the American College of Cardiology 61.13 (2013): 1409-1420.
Kim, et al., "Patient-Specific Modeling of Blood Flow and Pressure in Human Coronary Arteries". Annals of Biomedical Engineering, vol. 38, No. 10, Oct. 2010, pp. 3195-3209.
Taylor, et al., "Patient-Specific Modeling of Cardiovascular Mechanics", vol. 11: 109-134, Aug. 2009.
Indolfi, et al., "Instantaneous wave-Free Ratio (iFR) and Gradient (iFG): new promising adenosine-independent alternative to fractional flow reserve. Preliminary results from the FORECAST Study", www.jacc.tctabstracts2012.com, Oct. 2012.

* cited by examiner

IFR-CT

CROSS REFERENCE TO RELATED APPLICATIONS

This application is the U.S. National Phase application under 35 U.S.C. § 371 of International Application No. PCT/IB2016/050043, filed Jan. 6, 2016, published as WO 2016/113646 on Jul. 21, 2016, which claims the benefit of U.S. Provisional Patent Application No. 62/103,721 filed Jan. 15, 2015. These applications are hereby incorporated by reference herein.

FIELD OF THE INVENTION

The following generally relates to estimating the instantaneous wave-free ratio or instant flow reserve (iFR) metric for a stenosis in a vessel based on image data and is described with particular application to computed tomography (CT).

BACKGROUND OF THE INVENTION

Fractional flow reserve (FFR) is a metric that has been used to indicate a functional significance of a coronary artery stenosis. It has been used with interventional cardiology procedures to measure pressure differences across the coronary artery stenosis to determine whether a stenosis impedes blood flow and hence oxygen delivery to the heart muscle, which may result in myocardial ischemia. FFR is a ratio of a pressure Pd behind a stenosis relative to a pressure Pin before the stenosis, or Pd/Pin, which is a ratio of maximum blood flow distal to a stenotic lesion to normal maximum flow in the same vessel. FFR is performed during coronary catheterization. For this, a catheter is inserted into the femoral or radial arteries using a sheath and guidewire. FFR uses a small sensor on the tip of the wire to measure pressure, temperature and flow to determine the exact severity of the lesion. This is done during maximal blood flow (hyperemia). A pullback of the pressure wire is performed, and pressures are recorded across the vessel.

Instantaneous wave-free ratio or instant flow reserve (iFR) is another measurement that can be used to indicate a functional significance of a coronary artery stenosis. iFR is defined as the ratio of Pd to Pin over a specific period in diastole referred to as "the wave-free period." During this wave-free period, the competing forces (waves) that affect coronary flow are quiescent, meaning pressure and flow change in a similar way, which makes their ratio (i.e. resistance) almost constant, compared to the rest of the cardiac cycle. iFR is also performed during cardiac catheterization using invasive coronary pressure wires which are placed in the coronary arteries that are to be assessed. Both FFR and iFR are values in a range of zero (0) to one (1), where a higher value indicates a non or less-significant stenosis and a lower value indicates a more significant stenosis. Unfortunately, both FFR and iFR are invasive procedures and thus are susceptible to complications ranging from infection to death.

FFR-CT is a non-invasive procedure used to provide an estimation of FFR using a computational fluid dynamic (CFD) simulation on coronary geometry that is extracted from a non-invasively cardiac CT study. Unfortunately, CFD based FFR estimation requires a complicated dynamic simulation with many transitional effects occurred during cardiac contraction and relaxation and a complicated model with many uncertainties which, may lead to high estimation error.

SUMMARY OF THE INVENTION

Aspects of the present application address the above-referenced matters and others.

According to one aspect, a method includes for non-invasively determining an instantaneous wave-free ratio metric includes receiving electronically formatted image data generated by an imaging system. The image data includes voxels with intensities representative of a vessel with a stenosis. The method further includes computing peripheral resistances of outlets of the vessel from the image data. The method further includes calculating a stenosis resistance of the stenosis between an inlet of the vessel inlet and the outlets of the vessel based on a set of boundary conditions and a computational fluid dynamics algorithm. The method further includes calculating the instantaneous wave-free ratio metric. The metric is a numerical value, based on the stenosis resistance and generating a signal indicative of the calculated instantaneous wave-free ratio metric.

In another aspect, a system for non-invasively determining an instantaneous wave-free ratio metric a parameter determiner configured to compute peripheral resistances of outlets of a vessel from image data. The system further comprises a stenosis resistance determiner configured to calculate a stenosis resistance of a stenosis of the vessel between an inlet of the vessel inlet and the outlets of the vessel based on a set of boundary conditions and a result of a computational fluid dynamics algorithm. The system further comprises an iFR determiner configured to calculate the instantaneous wave-free ratio metric, wherein the metric is a numerical value, based on the stenosis resistance, and generate a signal indicative of the calculated instantaneous wave-free ratio metric.

In another aspect, a computer readable storage medium is encoded with computer readable instructions, which, when executed by a processor of a computing system, causes the processor to: calculate an iFR metric only from non-invasively determined parameters, which are determined non-invasively based on computed tomography image data and a computational fluid dynamic algorithm Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
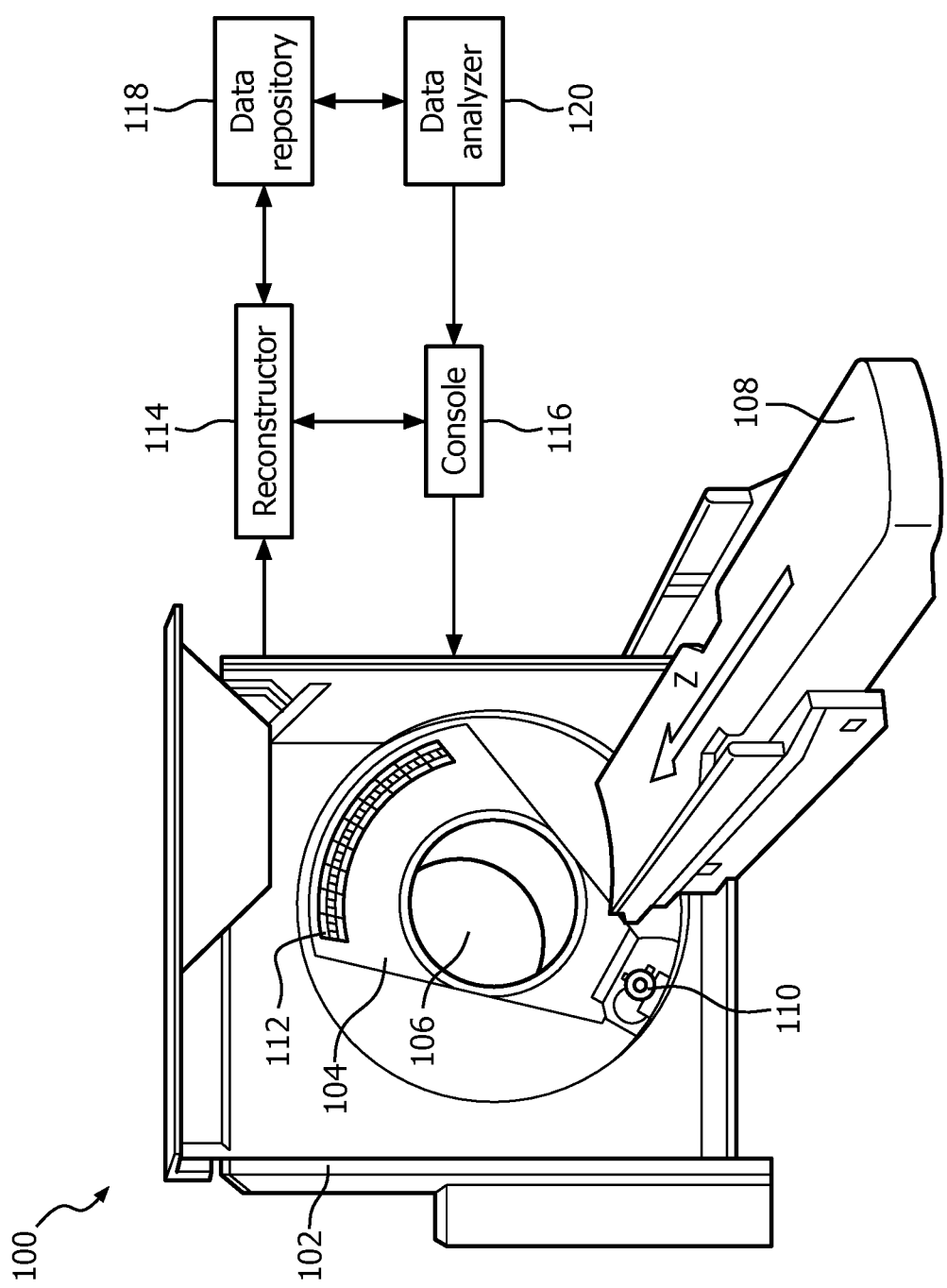
FIG. 1 schematically illustrates an imaging system in connection with a data analyzer.

The following describes a non-invasive approach for estimating an iFR metric based on a specific coronary geometry estimated from cardiac CT scan. FIG. 1 schematically illustrates an imaging system 100 such as a CT scanner. The imaging system 100 includes a generally stationary gantry 102 and a rotating gantry 104, which is rotatably supported by the stationary gantry 102 and rotates around an examination region 106 about a z-axis.

A radiation source 110, such as an x-ray tube, is rotatably supported by the rotating gantry 104, rotates with the rotating gantry 104, and emits radiation that traverses the examination region 106. A radiation sensitive detector array 112 subtends an angular arc opposite the radiation source 110 across the examination region 106. The radiation sensitive detector array 112 detects radiation traversing the examination region 106 and generates projection data, or a signal indicative thereof for each detected photon.

A reconstructor 114 reconstructs the projection, generating volumetric image data indicative of a scanned portion of a subject or object located in the examination region 106. An operator console 116 includes a human readable output device such as a monitor and an input device such as a keyboard, mouse, etc. Software resident on the console 116 allows the operator to interact with and/or operate the scanner 100 via a graphical user interface (GUI) or otherwise.

A subject support 119, such as a couch, supports an object or subject in the examination region 106. A data repository 118 stores electronically formatted data, including the volumetric image data and/or the projection data. Examples of the data repository include a picture archiving and communication system (PACS), radiology information system (RIS), a hospital information system (HIS), an electronic medical record (EMR), a database, a server, etc.

A data analyzer 120 is configured to process image data representing a vessel(s) (e.g., coronary arteries) of interest that includes a stenosis, wherein the image data is acquired during the wave-free period of diastole. As described in greater detail below, such processing includes estimating peripheral resistances at the vessel outlets using CFD simulation and determining an iFR metric based thereon. In the diastolic period, both the coronary pressure and velocity decrease monotonically. The temporal pressure and velocity at the diastolic wave free period can be approximated using linear function. The wave-free peripheral resistance at each vessel outlet, defined by the ratio between the pressure and velocity, is approximately constant and can be estimated. CFD simulation during the wave-free period of diastole provides a fast estimation of the functional significance of a stenosis. The resulting CT based iFR (iFR-CT) metric leads to a more robust and non-invasive estimation of the functional significant of a stenosis.

The data analyzer 120 can be implemented with one or more processors (e.g., a microprocessor, a central processing unit, etc.) of one or more computing systems that execute one or more computer readable instructions stored in one or more non-transitory computer readable storage mediums, such as physical memory. At least one instruction processed by the one or more processors may additionally or alternatively be carried by a carrier wave, a signal and/or other transitory medium. The data analyzer 120 can be part of the console 116, a computing system external to the imaging system 100, distributed across computing systems, a combination thereof, etc.

Figure 2:
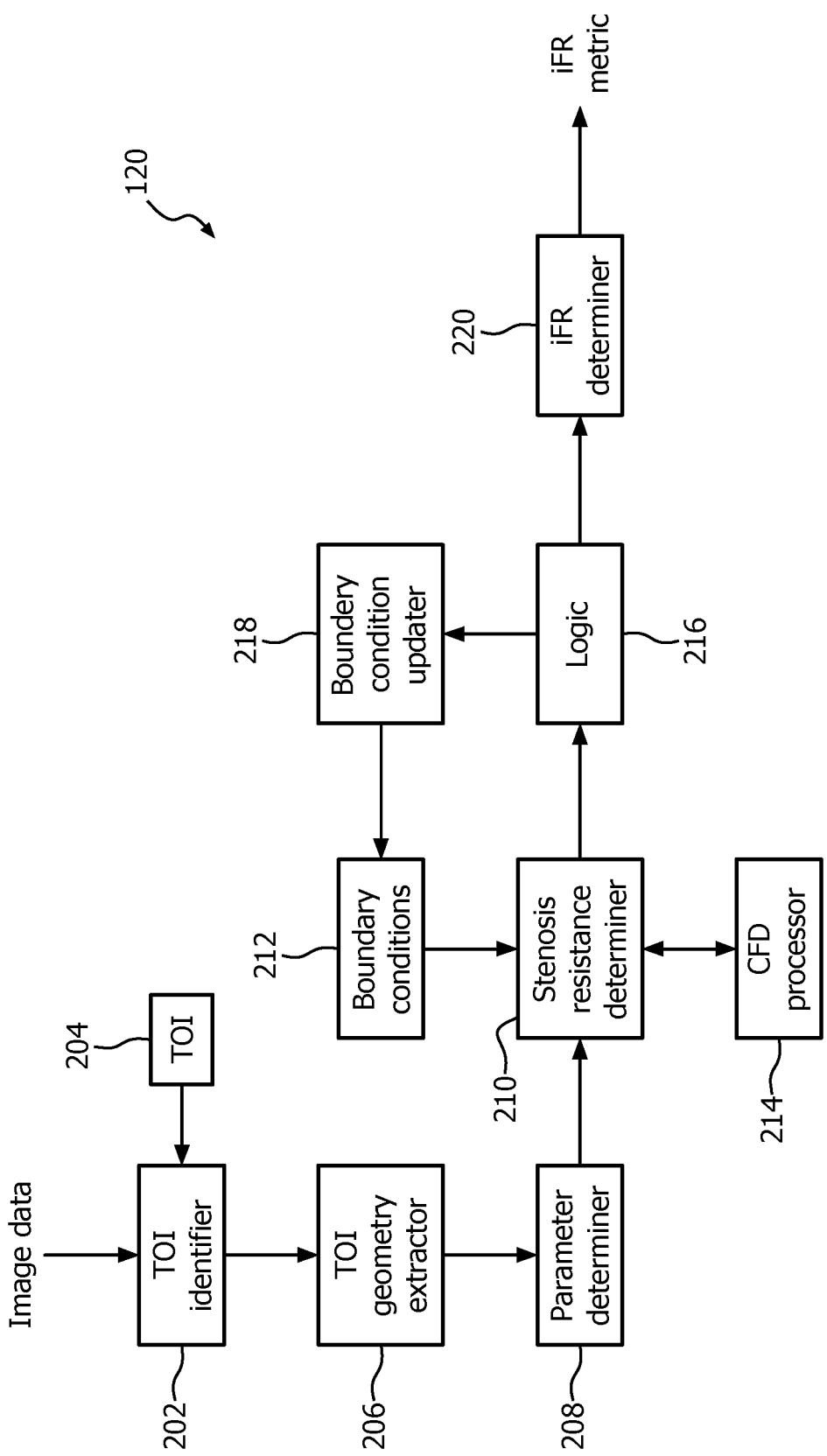
FIG. 2 illustrates an example of the data analyzer of FIG. 1.

FIG. 2 illustrates an example of the data analyzer 120.

A tissue of interest (TOI) identifier 202 obtains, as input, including image data with voxels with intensities representative of tissue of interest (TOI) 204 and identifies the tissue of interest 204 in the image data. The tissue of interest 204 can be predetermined or identified by a signal indicative of a user selected tissue of interest, a default tissue of interest, etc. The TOI identifier 202 can employ automatic and/or manual approaches to identify the tissue of interest. An example of tissue of interest is tubular tissue such as a vessel with a stenosis. However, the tissue of interest can be other tissue.

A TOI geometry extractor 206 extracts geometrical information from the identified tissue of interest. The TOI identifier 202 can employ automatic and/or manual approaches to extract the geometrical information. By way of example, the extraction may include employing segmentation with active-contours and level-sets tuned for coronary vessels where the tissue of interest is the coronary vessels, followed by optional additional manual editing to produce high quality segmentation. From this and/or other extraction, geometry of interest (e.g., vessel diameter) of the coronary vessels can be determined.

A parameter determiner 208 determines at least one parameter based on the extracted geometry of interest. The illustrated parameter determiner 208 is configured to estimate a peripheral resistance at a vessel outlet. For this, the parameter determiner 208 can utilize physiological rules in distributing blood to the tissue and take into account the characteristics and limits of cardiac CT scan. For example, since the distal part of the coronary arteries maybe under the resolution cut off, a representative cut point can be found such that the outlet area is proportional to a fraction of blood supplied to the region being fed by this artery.

Examples rules for the cut point selection include: after the stenosis; shortly after the last bifurcation; represent the area of the vessel; and invariant to different segmentors. Other and/or different, more or less, etc. rules are also contemplated herein. The wave-free peripheral resistance of a specific outlet can be estimated, with respect to the main coronary branch, based on scaling laws, as shown in EQUATION 1:

$$R_i = R_{main}\left(\frac{D_i}{D_{main}}\right)^{-1/3}, \quad \text{EQUATION 1}$$

where $R_i$ represents the wave-free peripheral resistance of an outlet of interest, $R_{main}$ represents a resistance of the main coronary branch, $D_i$ represents a diameter at the outlet of interest, and $D_{main}$ represents the diameter at the main coronary branch. $R_{main}$ can be estimated through machine learning and/or other approaches.

A stenosis resistance determiner 210 determines a resistance of the stenosis in the image data. In one example, the stenosis resistance determiner 210 determines a resistance r of the stenosis between each inlet and each outlet based on boundary conditions 212 and EQUATION 2:

$$r \approx \frac{P_{inlet} - P_{outlet}(CFD(P_{inlet}, v_{outlet}))}{v_{outlet}} \quad \text{EQUATION 2}$$

where $P_{inlet}$ is a boundary condition and represents a pressure at the inlet, $v_{outlet}$ is a boundary condition and represents a velocity at the outlet, $P_{outlet}$ represents a pressure at the outlet, which is estimated based on CFD ( ), which is a computational fluid dynamic algorithm that takes as an input $P_{inlet}$ and $v_{outlet}$ In one instance, the initial boundary conditions for the outlet velocity and inlet pressure are set as normal average velocity and pressure values, respectively. (e.g., outlet velocity=40 cm/s, and inlet pressure=100 mmHg), The boundary condition of the outlet pressure can be set as zero gradient, and the values are obtained in vis CFD.

A CFD processor 214 performs the computational fluid dynamic (CFD) simulation, for example, using partial-differential-equations. Generally, CFD is a fluid mechanics approach that uses numerical methods and/or algorithms to solve and analyze problems that involve fluid flows. The CFD processor 214 performs the calculations with surfaces defined by boundary conditions. The output, in one instance, includes full volumetric information of pressure at all points, for example, the pressures at the outlet. CFD simulation during the diastolic wave-free period is less complex than during other periods.

Using EQUATION 2, the resistance of the stenosis r can be estimated iteratively. The following illustrates an example iterative approach over n (n=1, . . . N) iterations. The boundary conditions $P_{inlet}$ and $v_{outlet}$ are initialized. During each iteration, a CFD simulation is performed with the current boundary conditions, generating $P_{outlet}^{(n)}$. An updated estimated resistance $r^{(n+1)}$ is calculated as shown in EQUATION 3:

$$r^{(n+1)} = \frac{P_{inlet} - P_{outlet}^{(n)}}{v_{outlet}^{(n)}}.\qquad\text{EQUATION 3}$$

Logic 216 checks to see if stopping criteria has been satisfied. In one instance, the stopping criteria is based on minimizing a sum of squares difference (SSD) between the current and previous resistances as shown in EQUATION 4:

$$\sum_{All\_outlets} SSD(R_c, R_p),\qquad\text{EQUATION 4}$$

where $R_p$ are target resistances, which are learned using statistics on a database and machine learning techniques, $R_c$ represent the actual (current) resistances at the outlets (during the optimization) and are calculated at each CFD iteration using the outlet's velocity and outlet's pressure. For a given outlet: $R_c = P_{outlet}/V_{outlet}$, where $P_{outlet}$ is obtained from the CFD iterations. The stopping criteria in EQUATION 4 is convergence of $R_c$ with $R_p$.

If the stopping criteria is not satisfied, a boundary condition updater 218 updates the boundary condition $v_{outlet}$ based on the calculated stenosis resistance $r^{(n)}$ as shown in EQUATION 5:

$$v_{outlet}^{(n+1)} = \frac{P_{inlet}}{R_i + r^{(n)}},\qquad\text{EQUATION 5}$$

and EQUATIONS 2, 3 and 4 are performed again. In EQUATION 5, R refers to the peripheral resistance at outlet i and r denotes the resistance of a stenosis between the inlet and each outlet. If there is no stenosis, r~=0.

If the stopping criteria is satisfied, an iFR determiner 220 determines an iFR based on the calculated stenosis resistance. In general, an iFR metric is estimated after the resistances $R_i$ reached their target values. The iFR metric can be estimated as shown in EQUATION 6:

$$iFR = \frac{Pd}{P_a},\qquad\text{EQUATION 6}$$

where, $P_a$ is the inlet pressure (or the aortic pressure) and Pd is the simulated pressure-distal to a stenosis in question.

The foregoing allows non-invasive, robust, accurate and fast simulation. Furthermore, the level of uncertainty in modeling the FFR-CT is much larger than in estimating iFR-CT, and simulating iFR (performed at the quiet phase) is much simpler than CFD based FFR estimation. As such, iFR-CT leads to a more robust non-invasive estimation of the functional significant of a stenosis. Moreover, using the approached described herein, the iFR estimation is accelerated by order of magnitude, e.g., from five (5) minutes to ten (10) seconds.

Figure 3:
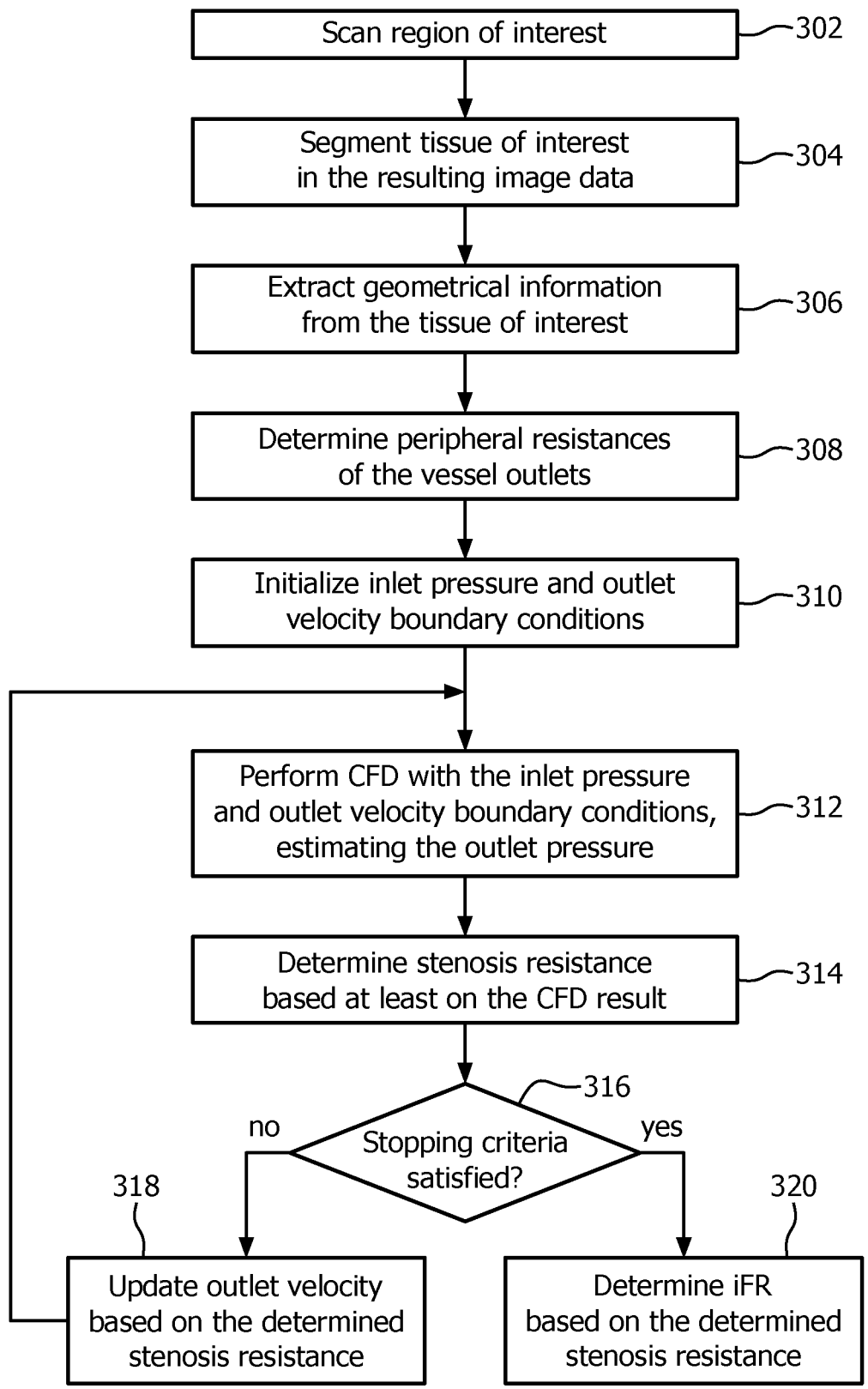
FIG. 3 illustrates an example method for determining an iFR metric.

FIG. 3 illustrates an example method for determining an iFR metric.

It is to be appreciated that the ordering of the above acts is not limiting. As such, other orderings are contemplated herein. In addition, one or more acts may be omitted and/or one or more additional acts may be included.

At 302, a region of a subject is scanned.

At 304, tissue of interest such as a coronary artery with a stenosis is segmented in image data from the scan.

At 306, geometrical information such as vessel diameter, vessel radius, etc. is extracted from the tissue of interest.

At 308, peripheral resistances at the coronary artery vessel outlets are determined based on the geometrical information.

At 310, inlet pressure and outlet velocity boundary conditions are initialized.

At 312, a CFD is performed using the inlet pressure and outlet velocity boundary conditions, estimating the outlet pressure.

At 314, a stenosis resistance is calculated based on the inlet pressure, the outlet velocity, and the estimated outlet pressure.

At 316, stopping criteria is check.

If the stopping criteria is not satisfied, then at 318 the outlet velocity is updated based on the calculated stenosis resistance, and acts 312-316 are repeated.

If the stopping criteria is satisfied, then at 320 an iFR metric is estimated.

The iFR metric can be saved to non-transitory memory, visually presented, processed, etc. As discussed herein, the iFR indicates a functional significance of a coronary artery stenosis such as a likelihood a stenosis will impedes oxygen delivery to the heart muscle.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method for non-invasively determining an instantaneous wave-free ratio metric by a data analyzer, comprising:
    receiving electronically formatted image data generated by an imaging system during a wave-free period of diastole, wherein the image data includes voxels with intensities representative of a vessel with a stenosis;
    computing peripheral resistances of outlets of the vessel from the image data;
    calculating a stenosis resistance of the stenosis between an inlet of the vessel and the outlets of the vessel based on a set of boundary conditions, a computational fluid dynamics algorithm and the peripheral resistances;
    calculating the instantaneous wave-free ratio metric, wherein the metric is a numerical value that is based on the stenosis resistance; and
    generating a signal indicative of the calculated instantaneous wave-free ratio metric.

2. The method of claim 1, further comprising:
    segmenting the vessel from the image data;
    determining a vessel diameter of an outlet of the vessel from the segmented image data;
    determining a branch diameter of a main coronary branch from the segmented image data;
    estimating a branch resistance of main coronary branch using machine learning; and
    wherein the peripheral resistances are computed based on the vessel diameter, the branch diameter, and the branch resistance.

3. The method of claim 2, wherein the peripheral resistances are computed as the branch resistance scaled by a ratio of the vessel diameter to the branch diameter.

4. The method of claim 3, wherein the peripheral resistances are computed as the branch resistance scaled by a cubed root of a ratio of the vessel diameter to the branch diameter.

5. The method of claim 1, wherein the set of boundary conditions includes a pressure at an inlet of the vessel and a velocity at an output of the vessel.

6. The method of claim 5, wherein the computational fluid dynamics algorithm computes an estimated pressure of the outlet of the vessel using the pressure at the inlet and the velocity at the output as input parameters.

7. The method of claim 6, wherein calculating the stenosis resistance includes iteratively calculating the stenosis resistance by:
    initializing the boundary conditions;
    performing the computational fluid dynamics algorithm using the boundary conditions to compute the estimated pressure of the outlets;
    estimating an updated stenosis resistance; and
    performing a second iteration in response to the updated stenosis resistance not satisfying a predetermined stopping criterion.

8. The method of claim 7, wherein the predetermined stopping criterion includes minimizing a sum of square differences between the previous and the current stenosis resistances.

9. The method of claim 7, wherein the second iteration comprises:
    computing an updated velocity at the outlet based on the updated stenosis resistance;
    performing the computational fluid dynamics algorithm using the pressure at the inlet and the updated velocity at the outlet;
    estimating a second updated stenosis resistance; and
    performing another iteration in response to the second updated stenosis resistance not satisfying the predetermined stopping criterion.

10. The method of claim 7, further comprising:
    computing the instantaneous wave-free ratio metric based on the stenosis resistance in response to the updated stenosis resistance satisfying the predetermined stopping criterion.

11. The method of claim 1, further comprising:
    generating a classification signal indicating whether the metric is greater or less than a predetermined threshold, wherein a metric value above the threshold indicates a first level of stenosis and a metric value below the threshold indicates a second level of stenosis, wherein the first level of the stenosis is more severe than the second level of the stenosis.

12. A system for non-invasively determining an instantaneous wave-free ratio metric, comprising:
    a storage medium; and
    at least one processor configured to:
        calculate peripheral resistances of outlets of the vessel from image data generated by an imaging system during a wave-free period of diastole, wherein the image data includes voxels with intensities representative of a vessel with a stenosis;
        calculate a stenosis resistance of the stenosis of the vessel between an inlet of the vessel and the outlets of the vessel based on a set of boundary conditions, a result of a computational fluid dynamics algorithm and the peripheral resistances;
        calculate the instantaneous wave-free ratio metric, wherein the metric is a numerical value that is based on the stenosis resistance; and
        generate a signal indicative of the calculated instantaneous wave-free ratio metric.

13. The system of claim 12, wherein the at least one processor is further configured to:
    identify the vessel in the image data;
    determine a vessel diameter of an outlet of the vessel and a branch diameter of a main coronary branch from the image data and a branch resistance of main coronary branch using machine learning; and
    compute the peripheral resistances of outlets of a vessel from image data based on the vessel diameter, the branch diameter, and the branch resistance.

14. The system of claim 13, wherein the peripheral resistances are computed as the branch resistance scaled by a ratio of the vessel diameter to the branch diameter.

15. The system of claim 13, wherein the peripheral resistances are computed as the branch resistance scaled by a cubed root of a ratio of the vessel diameter to the branch diameter.

16. The system of claim 12, wherein the set of boundary conditions includes a pressure at an inlet of the vessel and a velocity at an output of the vessel.

17. The system of claim 16, wherein the stenosis resistance is calculated as a ratio of the pressure at the inlet less the pressure at the outlet to the velocity at the outlet.

18. The system of claim 12, wherein the stenosis resistance is iteratively determined.

19. The system of claim 18, wherein each iteration an updated stenosis resistance is calculated, and another iteration is performed only if a sum of squares between the updated stenosis resistance and a previous stenosis resistance does not satisfy stopping criterion.

20. A non-transitory computer readable storage medium having one or more executable instructions stored thereon, which, when executed by at least one processor, cause the at least one processor to perform a method for non-invasively determining an instantaneous wave-free ratio metric by a data analyzer, the method comprising:

receiving electronically formatted image data generated by an imaging system during a wave-free period of diastole, wherein the image data includes voxels with intensities representative of a vessel with a stenosis;

computing peripheral resistances of outlets of the vessel from the image data;

calculating a stenosis resistance of the stenosis between an inlet of the vessel and the outlets of the vessel based on a set of boundary conditions, a computational fluid dynamics algorithm and the peripheral resistances;

calculating the instantaneous wave-free ratio metric, wherein the metric is a numerical value that is based on the stenosis resistance; and generating a signal indicative of the calculated instantaneous wave-free ratio metric.

* * * * *